United States Patent
Piccolo et al.

(10) Patent No.: US 6,593,478 B2
(45) Date of Patent: Jul. 15, 2003

(54) STEREOSPECIFIC HYDROLYSIS OF OPTICALLY ACTIVE ESTERS

(75) Inventors: Oreste Piccolo, Sirtori (IT); Roberto Castagnani, Recanati (IT); Paolo De Witt, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/168,792

(22) PCT Filed: Dec. 15, 2000

(86) PCT No.: PCT/IT00/00521

§ 371 (c)(1), (2), (4) Date: Jun. 24, 2002

(87) PCT Pub. No.: WO01/47908

PCT Pub. Date: Jul. 5, 2001

(65) Prior Publication Data

US 2003/0032818 A1 Feb. 13, 2003

(30) Foreign Application Priority Data

Jun. 19, 1999 (EP) .......................................... 0 924 206 A
Dec. 23, 1999 (IT) ........................................ RM99A0787

(51) Int. Cl.$^7$ ...................... C07D 307/06; C07D 307/20
(52) U.S. Cl. ....................................... 549/313; 549/475
(58) Field of Search ................................. 549/313, 475

(56) References Cited

U.S. PATENT DOCUMENTS 5,599,978 A    2/1997   Giannessi et al.

FOREIGN PATENT DOCUMENTS

EP    0 924 206 A    6/1999

OTHER PUBLICATIONS

Tanaka A et al; "A Novel Synthesis of (R)– And (2)–4–Hydroxytetrahydrofuran–2–Ones" Synthesis, DE, Georg Thieme Verlag, Stuttgart, 1987, pp. 570–572, XP002042273.

*Primary Examiner*—Taofiq Solola
(74) *Attorney, Agent, or Firm*—Nixon & Vanderhye P.C.

(57) ABSTRACT

A new, more efficient and highly stereospecific process is described for the preparation of compounds with general formula (R)-(I) and of absolute configuration (R), where the groups M, W, Q and $Q_1$ are as defined in the description, starting from compounds of absolute configuration (S) by hydrolysis, in the presence of acids, of the corresponding esterified derivatives. The (R)-(I) products obtained with the process described herein are chiral synthons useful for the production of enanthiomerically pure drugs. The preparation of (R)-carnitine is also provided.

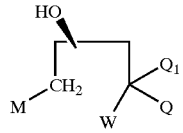

(R)-(I)

8 Claims, No Drawings

STEREOSPECIFIC HYDROLYSIS OF OPTICALLY ACTIVE ESTERS

This application is a 371 of PCT/IT00/00521 filed Dec. 15, 2000, which designated the U.S.

The invention described herein relates to a stereospecific process for the preparation of compounds of general formula (R)-(I) and of absolute configuration (R)

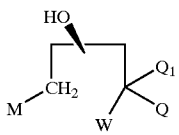

(R)-(I)

where:

Q and $Q_1$ are hydrogen atoms; or,

Q and $Q_1$ taken together form the =O group;

M is the trimethylammonium group or an -OZ group;

W is a group selected from —OH, -OL, or -OZ, or

M and W, taken together, form the group —O—, so that the compound of formula (R)-(I) is the compound of formula (R)-(A)

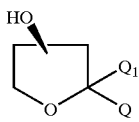

L is a $C_1$–$C_6$ linear or branched alkyl or a benzyl group;

-OZ group is the residue of an ester of a sulphuric, phosphonic or phosphoric acid selected from:

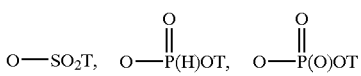

where:

T is $C_1$–$C_{10}$ linear or branched alkyl, optionally substituted with one or more halogen groups, such as, for example, trihalomethyl; or T is an aryl group, such as, for example, phenyl, tolyl, halophenyl or nitrophenyl.

The compounds of formula (R)-(I) can be prepared starting from (S)-(II) derivatives

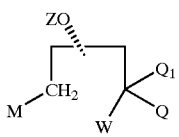

(S)-(II)

where:

Q, $Q_1$, M, W and -OZ have the above defined meanings.

Derivatives of formula (S)-(II) can be prepared starting from (S)-(I) compounds according to the following reaction scheme 1:

SCHEME 1

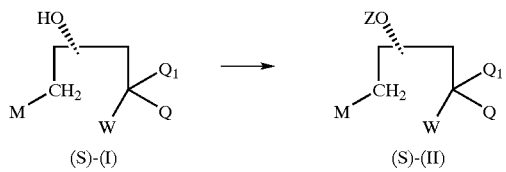

where Q, $Q_1$, M, W and -OZ have the above defined meanings, which comprises an esterification reaction of the hydroxyl group of the (S)-(I) compound to yield derivative (S)-(II), according to known methods.

The compound of formula (S)-(I) where Q and $Q_1$ taken together form the =O group, M is the trimethylammonium group, W is —OH and the —OH group is in position β with respect to the -$CQQ_1$ group, is (S)-carnitine, which is a discard product of the process for the preparation of (R)-carnitine. The compound of formula (S)-(I), wherein Q and $Q_1$, taken together, form the group =O, M and W, taken together, are the group —O— and the —OH group is in position β with respect to the group -$CQQ_1$, is obtained easily and at low cost, using the process described in Italian patent IT 1276207, starting from (S)-carnitine, whereas the compound of formula (S)-(I), where Q and $Q_1$ are hydrogen atoms, M and W, taken together, are the group —O— and the —OH is in position β with respect to the group -$CQQ_1$, is obtained, for example, following the process described in Organic Synthesis (38) 1958, 37–38.

Compounds of formula (R)-(I) are versatile chiral intermediates used in various industrial synthesis processes. For example, the compound of formula (R)-(I), in which Q and $Q_1$, taken together, form the =O group, M and W, taken together, are the group —O— and the group —OH is in position β with respect to the group -$CQQ_1$, can be used in the synthesis of beta-lactam antibiotics, in the well-known anticonvulsant GABOB ((R)-4-amino-3-hydroxy-butyric acid), and in the synthesis of (R)-carnitine. (R)-carnitine can be even prepared from the discard product (S)-carnitine.

Despite the acknowledged usefulness of compounds of formula [R]-[I] as versatile intermediates, to date no satisfactory processes have been developed to enable them to be synthesised on an industrial scale.

In fact, the synthesis of (R)-(I) compounds, where Q and $Q_1$, taken together, form the =O group, M and W, taken together, are the group —O— and the —OH group is in the β position with respect to the group -$CQQ_1$, starting from L-ascorbic acid, requires as many as seven steps with low yields (29%) (Tanaka, A.; Yamashita, K., *Synthesis,* 1987, 570–572).

The synthesis of (R)-(I) compounds where Q and $Q_1$ are hydrogen atoms, M and W, taken together, are the group —O— and the —OH group is in the β position with respect to the group -$CQQ_1$, starting from dimethyl-(R)-malate, entails a cumbersome reduction (practically impossible to implement on an industrial scale) with borane-dimethylsulphide complex, which is fraught with problems of safety and pollution (Saito, S.; Hasegawa, T.; Inaba, M.; Nishida, R.; Fujii, T.; Nomizu, S.; Moriwake, T., *Chem. Lett.,* 1984, 1389–1392).

Italian patent application RM95A000652 describes the synthesis of (S)-beta-hydroxy-gamma-butyrolactone starting from (S)-carnitine. With the method described in RM95A000652 it is also possible to prepare (R)-(I) compounds starting from (R)-carnitine. This process is clearly not economically advantageous since (R)-carnitine is a particularly valuable and expensive compound.

Italian patent application RM97A000780 describes the synthesis of (R)-(I) compounds using as the starting product (S)-(I) compounds where Q and $Q_1$ taken together form the =O group, M and W, taken together are the group —O— and the —OH group is in the β position with respect to the group -$CQQ_1$. This process is not advantageous in that involves a large number of steps and gives low yields.

It would therefore be advantageous to have a process for the preparation of (R)-(I) compounds which can be implemented on an industrial scale and which does not present the numerous serious drawbacks of the known methods: large number of steps, low yields, use of expensive, hazardous and/or polluting reactants.

A new process has now been found, and constitutes the subject matter of the invention described herein, for the preparation of compounds of formula (R)-(I) starting from derivatives of formula (S)-(II) that overcomes the technical problems encountered with the above-mentioned known processes.

The process according to the invention described herein can be represented schematically by means of scheme 2 here below:

SCHEME 2

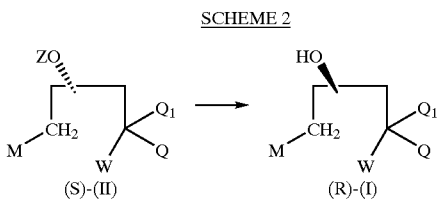

(S)-(II)    (R)-(I)

where:

the groups M, W, Z, Q and $Q_1$ are as above defined.

comprising reacting derivatives of formula (S)-(II) with an aqueous solution of a strong organic or inorganic acid at a temperature ranging from about 60 to about 100° C. and preferably from about 75 to about 85° C.

What is meant by strong organic or inorganic acid is any acid that has a negative pKa in relation to water (March Advanced Organic Chemistry fourth edition pp. 248–252).

Examples of such acids, though not exclusively these, are hydrochloric acid, hydrobromic acid, hydroiodic acid, nitric acid, phosphoric acid, methanesulphonic acid, sulphuric acid, trifluoromethanesulphonic acid, or benzenesulphonic acid. A convenient molar ratio of acid to substrate is ≧1, and preferably ≧2.

The amount of water utilised in the process according to the invention is the minimum amount possible. The optimal ratio of ester to water, in the presence of strong acid, is easily calculated on the basis of hot solubility tests.

The reaction is conducted at a temperature ranging from about 60 to about 100° C., and preferably from about 75 to about 85° C. The person skilled in this field will understand that the term about, relating to the above mentioned temperature range means that the temperature can be kept around the indicated term within a range which does not substantially change the reaction conditions given at the indicated temperature level, such as, for instance, the reaction conveniently proceeds, there is no unwanted degradation of products or reactants, the limit can also be given by the boiling point of the solvent.

A further object of the invention described herein is a process for the preparation of compounds of formula (R)-(I) starting from (S)-(I) compounds according to scheme 3 here below:

SCHEME 3

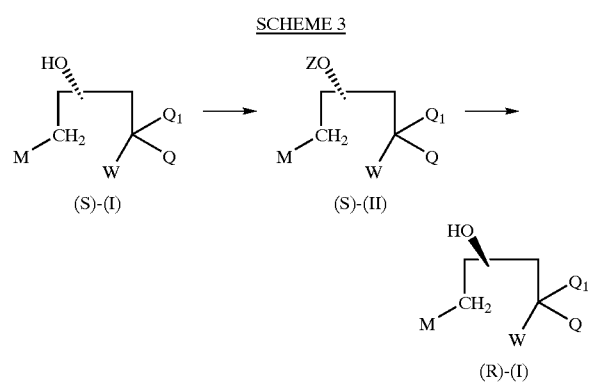

(S)-(I)    (S)-(II)

(R)-(I)

where:

the groups M, W, Z, Q and $Q_1$ are as defined above comprising:

b) esterification of the hydroxyl group of compound (S)-(I) to give the formula (S)-(II) derivative;

c) reacting the derivative of formula (S)-(II) obtained in a) with an aqueous solution of a strong organic or inorganic acid at a temperature ranging from about 60 to about 100° C.

All meanings, conditions and explanations for the process above disclosed in scheme 3 are essentially the same as the ones explained for the process disclosed in the scheme 2 above.

Thanks to the process according to the invention, in its various embodiments, it is now possible to accomplish inversion of the configuration of the asymmetrical carbon atom with a high degree of stereospecificity and high yields, and in a much more practicable manner than when using any of the known techniques adopted to date.

Table 1 here below presents the results obtained in the conversion of the derivative (S)-3-mesyloxy-4-butyrolactone (III), with an enantiomeric excess (e.e.) >99%, to (R)-3-hydroxy-butyrolactone in which molar ratios of acid to substrate ranging from 0 to 2 were used.

TABLE 1

Hydrolysis of (S)-3-mesyloxy-4-butyroLactone in water at 80–85° C.

| Molar ratio of acid added to (S)-3-mesyloxy-4-butyrolactone (III) | Acid Utilised | (R)-3-hydroxy-butyrrolactone (e.e. %) |
|---|---|---|
| 0 | None | 67.2 |
| 0.2 | HCl or $CH_3SO_3H$ | 78.7–81.5 |
| 1 | HCl or $CH_3SO_3H$ or $HNO_3$ | 84–87 |
| 2 | HCl or $HNO_3$ | 94.6–96.0 |

The data reported in Table 1 show that the convenient molar ratio of acid to substrate is ≧1, and preferably ≧2.

A number of examples are given here below which further illustrate the invention.

EXAMPLE 1

Preparation of (R)-3-hydroxy-4-butyrolactone.

10 g of (S)-3-mesyloxy-4-butyrolactone, prepared according to the process described in RM97A000780 starting from (S)-3-hydroxy-4-butyrolactone with e.e. >99%, were suspended in $H_2O$ (0.2 L) and added with HCl 37% (11 g).

The mixture was heated to 80° C. for approximately 8 h and yielded (R)-3-hydroxybutyrolactone with 96% e.e. and 2-(5H)-furanone in a ratio of approximately 2:1, with almost total disappearance of the starting mesylate.

The mixture was then treated with NaOH 7% (70 ml), concentrated to dryness and extracted with acetone (0.2 L) to allow precipitation of the salts that are removed by filtration.

The mixture was concentrated again to yield a residue of 9.3 g.

A sample purified by chromatography on XAD 1600T resin, using $H_2O$ as the eluant yielded (R)-3-hydroxy-4-butyrolactone with a rotatory power of $[a]_D^{25}$+83 (c=1.2%, $CH_3OH$), e.e. 96% (75% yield).

EXAMPLE 2
Preparation of (R)-3-hydroxy-tetrahydrofuran.

Operating as in example 1, but using 2.7 g of (S)-3-mesyloxy-tetrahydrofuran prepared starting from (S)-3-hydroxy-tetrahydro-furan, with ≧99% e.e., (R)-3-hydroxy-tetrahydrofuran was obtained with a rotatory power of $[a]_D^{25}$-17.1 (c=2.5%, $CH_3OH$), e.e. 97%, with a 75% yield.

EXAMPLE 3
Preparation of (R)-Carnitine

To a mixture of (S)-mesyloxy carnitine methanesulfonate (13 g), prepared as in Angewandte Chemie Vol.33, N° 20, 1994, p.2076, in $H_2O$ (0.26 L) having e.e. >99%, $CH_3SO_3H$ (7.45 g) is added.

After heating at 80° C. for 24h the mixture is cooled at r.t. and eluted on IRA 410 (OH-form)(0.25 L).

The eluate (0.75 L) is concentrated and the residue, crystallised by isobutyl alcohol, gives (R)-Carnitine with 94% e.e. (yield 66%).

EXAMPLE 4
Preparation of (R)-3-hydroxytetrahydrofuran

To a mixture of (S)-1,2,4-trimesyloxy butane (10 g), prepared as in HETEROCYCLES vol.24 N° 5, 1986 p.1331, starting from (S)-1,2,4-butanetriol having e.e. >99%, in $H_2O$ (200 ml) $CH_3SO_3H$ (5.6g) is added.

The temperature is left to rise up to 80° C. and kept for 27h.

After cooling to r.t. the mixture is treated in batch with IRA 410 (OH-form) (0.2 L).

The resin is filtered off, and washed with $H_2O$; the filtrate gives, after distillation and chromatographic purification (R)-3-hydroxytetrahydrofuran with 94% e.e. (yield 54%).

EXAMPLE 5
Preparation of (R)-3-hydroxytetrahydrofuran

To a solution of (S)-3-hydroxytetrahydrofuran (5 g) having e.e. >99% in $CH_2Cl_2$ (100 ml) MsCl (7.8 g) is added and subsequently at 0–5° C. triethylamine (7 g).

The temperature is then left to rise up to r.t. and after 1 h is extracted with $H_2O$.

The organic phase is concentrated, gives an oil that is then treated with $H_2O$ (0.1 L) and $CH_3SO_3H$ (10.9 g).

After heating at 88–90° C. for 5h the mixture is cooled at r.t. and diluted with $H_2O$ (50 ml).

The obtained solution is eluted on IRA 410 (OH-form) (0.3 L) and the eluate gives after concentration under vacuum (R)-3-hydroxytetrahydrofuran with 88% e.e. (yield 77%).

What is claimed is:

1. A process for the preparation of a compounds of formula (R)-(I) from (S)-(II) according to the following reaction scheme:

where:
Q and $Q_1$ are hydrogen atoms; or,
Q and $Q_1$ taken together form the =O group;
M is a trimethylammonium group or an -OZ group;
W is a group selected from —OH, -OL, or -OZ, or
M and W, taken together, form the group —O—, so that the compound of formula (R)-(I) is the compound of formula (R)-(A)

L is a $C_1$–$C_6$ linear or branched alkyl or a benzyl group;
-OZ group is the residue of an ester of a sulphuric, phosphonic or phosphoric acid selected from:

$$O-SO_2T, \quad O-\overset{O}{\underset{\|}{P}}(H)OT, \quad O-\overset{O}{\underset{\|}{P}}(O)OT$$

where:
T is $C_1$–$C_{10}$ linear or branched alkyl, optionally substituted with one or more halogen groups, or T is an aryl group, comprising reacting a compound of formula (S)-(II) with an aqueous solution of a strong organic or inorganic acid which has a negative pKa in relation to water, at a temperature ranging from about 60 to about 100° C.

2. A process for the preparation of a compound of general formula (R)-(I) from (S)-(I) compounds according to the following reaction scheme Q and $Q_1$ are hydrogen atoms; or,
Q and $Q_1$ taken together form the =O group;
M is a trimethylammonium group or an -OZ group;
W is a group selected from —OH, -OL, or -OZ, or
M and W, taken together, form the group —O—, so that the compound of formula (R)-(I) is the compound of formula (R)-(A)

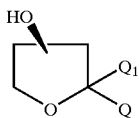

L is a $C_1$–$C_6$ linear or branched alkyl or a benzyl group;
-OZ group is the residue of an ester of a sulphuric, phosphonic or phosphoric acid selected from:

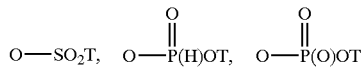

where:
T is $C_1$–$C_{10}$ linear or branched alkyl, optionally substituted with one or more halogen groups, or T is an aryl group;
said process compromising:
a) esterification of the hydroxyl group of compound (S)-(I) to give the compound of formula (S)-(II);
b) reacting the compound of formula (S)-(II) obtained in a) with an aqueous solution of a strong organic or inorganic acid at a temperature ranging from about 60 to about 100° C.

3. The process according to claim 1, in which the T group is methyl or trihatomethyl.

4. The process according to claim 1, in which the aryl is selected from the group consisting of phenyl, tolyl, halophenyl and nitrophenyl.

5. The process according to claim 1, in which the acid is selected from the group consisting of hydrochloric acid, hydrobromic acid, nitric acid, phosphoric acid, methanesulphonic acid, sulphuric acid, trifluoromethanesulphonic acid and benzenesulphonic acid.

6. The process according to claim 1, in which the molar ratio of the acid to the substrate is $\geq 1$.

7. The process according to claim 6, in which the molar ratio of acid to substrate is $\geq 2$.

8. The process according to claim 1, in which the temperature is from about 75 to about 85° C.

* * * * *

UNITED STATES PATENT AND TRADEMARK OFFICE
CERTIFICATE OF CORRECTION

PATENT NO. : 6,593,478 B2
DATED : July 15, 2003
INVENTOR(S) : Piccolo et al.

It is certified that error appears in the above-identified patent and that said Letters Patent is hereby corrected as shown below:

Title page,
Item [30], Foreign Application Priority Data, delete
"Jun. 19, 1999 (EP)……………..0 924 206 A"

Signed and Sealed this

Twenty-third Day of December, 2003

JAMES E. ROGAN
*Director of the United States Patent and Trademark Office*